(12) United States Patent
Goi et al.

(10) Patent No.: US 11,730,689 B2
(45) Date of Patent: Aug. 22, 2023

(54) PROCESS FOR TREATING HAIR

(71) Applicant: Davines S.p.A., Parma (IT)

(72) Inventors: Paolo Goi, Gorgonzola (IT); Margherita Nicoli, Parma (IT); Teresa Caccia, Parma (IT); Sonia Vaccaro, Parma (IT); Alessandra Mori, Cremona (IT)

(*) Notice: Subject to any disclaimer, the term of this patent is extended or adjusted under 35 U.S.C. 154(b) by 263 days.

(21) Appl. No.: 17/046,627

(22) PCT Filed: Apr. 4, 2019

(86) PCT No.: PCT/IT2019/050071
§ 371 (c)(1),
(2) Date: Oct. 9, 2020

(87) PCT Pub. No.: WO2019/198114
PCT Pub. Date: Oct. 17, 2019

(65) Prior Publication Data
US 2021/0161790 A1    Jun. 3, 2021

(30) Foreign Application Priority Data
Apr. 9, 2018  (IT) .................. 102018000004333

(51) Int. Cl.
| | | |
|---|---|---|
| *A61Q 5/02* | (2006.01) | |
| *A61Q 5/08* | (2006.01) | |
| *A61Q 5/12* | (2006.01) | |
| *A61K 8/49* | (2006.01) | |
| *A61K 8/362* | (2006.01) | |
| *A61K 8/46* | (2006.01) | |

(52) U.S. Cl.
CPC ............ *A61K 8/4986* (2013.01); *A61K 8/362* (2013.01); *A61K 8/46* (2013.01); *A61Q 5/02* (2013.01); *A61Q 5/08* (2013.01); *A61Q 5/12* (2013.01)

(58) Field of Classification Search
None
See application file for complete search history.

(56) References Cited

U.S. PATENT DOCUMENTS

| | | |
|---|---|---|
| 9,114,088 B2 † | 8/2015 | Konno |
| 9,326,926 B2 † | 5/2016 | Pressly |
| 9,713,583 B1 | 7/2017 | Pressly |
| 2005/0215622 A1 | 9/2005 | Majeed |
| 2010/0006449 A1 † | 3/2010 | Khan |
| 2011/0027327 A1* | 2/2011 | Albrecht ............... A61P 17/02 424/59 |
| 2016/0175229 A1 | 6/2016 | Delalande |

FOREIGN PATENT DOCUMENTS

| | | | |
|---|---|---|---|
| WO | WO-9416672 A1 * | 8/1994 | ............ A61K 8/02 |
| WO | 2016207840 | 12/2016 | |

OTHER PUBLICATIONS

Allured Business Media, Practical Modern Hair Science, Copyright 2012, www.Alluredbooks.com.†

* cited by examiner
† cited by third party

*Primary Examiner* — Jyothsna A Venkat
(74) *Attorney, Agent, or Firm* — Themis Law

(57) ABSTRACT

A method for treating hair includes applying to hair a cosmetic formulation having an active part with a binding and antioxidant action. The active part is liposol maleate or a mixture of liposol maleate and maleic acid, with a weight ratio from 5:95 to 95:5.

5 Claims, 2 Drawing Sheets

PROCESS FOR TREATING HAIR

BACKGROUND OF THE INVENTION

Hair consists of overlapped layers having different composition, even if keratin is its main component. The role of the external cuticle bed is to protect the internal fibers of hair; it is mainly correlated to the aesthetic properties of hair as softness, elasticity, compactness, brightness, etc.

When hair is healthy, the external behavior of the fiber is basically hydrophobic, not very polar, and neutrally charged.

The external cuticle part is the part more exposed to conditions able to deteriorate hair, particularly UV radiations, pollution but also chemical and mechanical treatments.

The protection of the hair stem is mainly due to the lipidic layer coating its surface. This lipidic layer is mainly composed of 18-Methyleicosanoic acid (18-MEA) covalently bound by formation of thioesters, esters and amides with cysteine, amine and alcohol groups of the underlying proteins.

The presence of 18-MEA acid is also showed in the area of the connection cuticle-cuticle (Cell Membrane Complex), where it takes part to the junction between cuticles.

However, this lipidic bed is prone to deteriorate by photo-oxidative and radical reactions due to exposition to UV radiations and air pollution that cause breaking of the thioester, ester or amide bonds producing the free acid and subsequently its removal from the external layer of hair.

Consequently, 18-MEA acid photo-oxidation increases the production of chemicals having acid sulfide groups, as mercaptan, sulfinate and sulfonate (particularly this last due to hair bleaching) by the photo-oxidation of the cysteine group remaining free after removal of the acid. All properties of virgin hair are changed; virgin hair properties, as above disclosed, are basically hydrophobic, not very polar, and neutrally charged while are now changed to a more hydrophilic, more polar and negatively charged fiber. By consequence, hair is more porous and impacting on a change of the mechanical and aesthetic properties of hair, now duller, less orderly and prone to breaking.

Moreover, removal of the surface lipidic layer by oxidation and photo-oxidation exposes the cuticle underlying layers to an exponential increase of degradation that can cause weakening until to breaking of hair.

It is known that, in the absence of the lipidic protective layer, the underlying layers Alpha-Layer and Beta-Layer (or exocuticle), both rich in cysteine, >30% the first and from 15 to 20% the second, are more easily subjected to the same photo-oxidative reaction or chemical aggression to which the external lipidic layer was previously subjected. It is worth to underline that hair having a low degree of pigmentation, particularly grey hair, is prone to deteriorate due to ultraviolet radiations in comparison with more pigmented hair.

The exposition to ultraviolet radiations and to external agents are not the only responsible of the hair state of health. It is known that 18-MEA acid can be subjected to the same degradation reactions due to alkaline treatment, bleaching treatment, permanent or straightening treatment.

Among the aggressive treatments above described, the alkaline treatment could be particularly frequent.

Hair is sensitive to a pH change, since it consists of many long protein chains made of amino acid units. These chains, or polymers, are bound to each other by means of 1) hydrogen bonds, 2) salt bridges between acid and basic groups, and 3) disulfide bonds. Water can affect by breaking hydrogen bonds in a reversible way. This enables to easily shape and arrange wet hair. When water vaporizes, hydrogen bonds are produced again in new positions, maintaining hair in the new style. In a very acid solution, for example at a pH of 1.0 to 2.0, both hydrogen bonds and salt bridges are broken. However, in these conditions the disulfide bonds can still keep together the protein chains in the hair swatch.

At a slightly alkaline pH of 8.5, some disulfide bonds are broken (see Dombrink et al., Chem. Matters 1983, page 8). Several washing steps with a slightly alkaline shampoo can damage hair more and more, breaking sulfide bonds. Therefore, the cuticle or the external surface of the hair swatch is getting frizzy and usually leaves hair swelled, entangled, and generally unmanageable. This is one of the causes for split ends.

When hair is dried up, it frequently remains in dry, wiry or frizzy conditions. Moreover, wiry hair catches the light in non-homogenous way giving rise to dull and not shine hair. Moreover, the frequently use of drying tools, can leave hair with an increased level of static electricity that may interfere with the combing and may produce stringy hair.

Heat and various reducing treatments are other processes that can lead to breakage of disulfide bonds in the hair.

Current compositions and methods for waving and straightening mammalian hair require reducing agents, as thioglycolic acid, particularly as ammonium salt, in order to break cysteine disulfide bonds in hair. When disulfide bonds are broken, hair is stressed to set the final style (for example smooth, wavy or curly) and disulfide bonds are restored. The process of oxidation in order to restore broken bonds, also called neutralization, can simply be obtained by exposing hair to atmospheric oxygen; however, this oxidation step can be very slow and unfeasible. Usually hydrogen peroxide or sodium bromate are used as oxidizing agents. However, the newly formed disulfide bonds are under stress to maintain the hair's new shape; thus, they easily break resulting in a reversion of the hair style over time. Moreover, the use of peroxides in the hair styling process can result in damaged hair, removal of non-natural color from hair, and/or leave frizzy hair. Furthermore, some latent reduced thiols may remain in hair even after oxidative treatment. Hair styling treatments with peroxides used in the neutralization process lead to the following reaction: 2 K—S—H+ $H_2O_2$ - - - →K—S—S—K+$2H_2O$ (Reaction a)

where K represents keratin in the hair. However, in the case where two K—S—H are not present for Reaction 1 to take place, it is believed that the following reaction takes place, which results in damaged hair.

$$K-S-H + H_2O_2 \rightarrow K-SO_2-OH \quad \text{(Reaction b)}$$

Many different processes useful to reduce these problems had been studied, for example an after-shampooing application of hair conditioning agents, as leave-on and rise-off products. Usually, the rinse-off conditionings restore the oily coating, particularly in the damaged part of hair where the cuticle is frizzy, since the conditioners are better linked to these parts.

However, too much conditioner or very heavy conditioner will make hair stickier, in this way attracting dirty particles, and often many shampoo treatments are necessary to remove the build-up. Usually the conditioners do not link thiol groups in hair and are not antioxidant agents, and consequently they do not extend the protective effect and cannot further prevent damages, particularly due to ultraviolet radiations and free radicals also produced by pollution.

The use of cationic polymers to make coacervates that can give some advantage to hair during conditioning is well known, as disclosed in WO 93/08787 (King et al.) and WO 95/01152 (Napolione et al.).

The commonly used deposition cationic polymers comprise natural polymers, as guar gum polymers modified by cationic groups. The selection of a cationic polymer guar having suitable charge density and molecular weight results in an appropriate deposition of conditioning agents when blended in a shampoo or a shower gel.

However, usually a large quantity of this cationic guar polymer must be placed on hair or on the skin. Moreover, this polymer is relatively expensive. By consequence, the addition of the cationic guar polymer can increase the manufacturing cost of the shampoo compositions thereof. Usually these shampoo compositions are useful for conditioning wet hair but are not able to leave a smoothness sensation on dry hair. Moreover, these conditioners do not bind the free thiol groups in hair and do not have antioxidant properties and, consequently, do not extend the protective effect and are not able to prevent further damages.

The document EP 3001809 (B), Liqwd, discloses a method for treating hair that requires the use of a primary diamine, both the amine groups being neutralized by reaction with maleic acid. A typical commercial formulation claimed by this patent is named Olaplex®. However, this formulation presents many drawbacks. For example, this formulation does not protect hair from damages due to oxidative and photo-oxidative damages. The protection of hair from the oxidation reactions that degrade in primis 18-MEA acid and then the cysteine groups that are exposed in the various keratin layers of hair, is made possible only providing chemical groups able to positively react during redox reactions. Then, it is very important for the hair protection to provide molecules able to bind in a covalent way to the cysteine groups and able to perform also an anti-radical, antioxidant reaction. The lack of protection from damages due to UV radiations does not allow for example to protect from hair cosmetic color fading during UV radiations exposition.

Hair dyes, using natural (henna) or synthetic pigments, are molecules characterized by the presence of different groups sensitive to free radicals. The exposition of the hair fibers to UV radiations without the presence of an antioxidant protection, is the cause of a progressive deterioration of tone and intensity of the initial coloration.

Finally, the action of restoring disulfide bonds in the formulations described in EP 3001809 (B) is made by means of two maleic acid salts that, by a Michael reaction, link the free thiol groups, whilst the primary diamine, salified with two maleic acid molecules, behaves like a bridge between the two ends linked to cysteine.

However, the bond between maleic acid and diamine is merely ionic and cannot be covalent; then it is sensitive to a ionic strength change related to the pH. Particularly, in alkaline environmental the ionic bond gets weak and the restoration of the disulfide bridges becomes less efficient.

Then, there is a need for hair formulations and treatments to give a stronger bond on the cysteine groups of keratin and preserve hair from further oxidative stress and give a better conditioning. Particularly, there is a need to provide hair with a long-term hydration sensation, a smoothness sensation, and manageable when dry.

There is also a need for hair formulations and treatments to repair free thiols remained in hair and at the same time to provide antioxidant protective action.

There is also a need for hair formulations and treatments that repair and/or strengthen damaged hair and rebuild stronger bonds in hair after a reducing treatment.

There is also a need to protect cosmetically colored hair from both the alkaline aggression of the coloring formulations and simultaneously from the degradation of the cosmetic color due to UV radiation exposition.

Therefore, it is an object of the present invention to provide improved formulations and methods for repairing and/or strengthen damaged hair and protect hair from oxidation reactions.

It is also an object of the present invention to provide formulations and methods for using these formulations to repair and/or strengthen hair after a washing, bleaching or reducing treatment.

SUMMARY OF THE INVENTION

Formulations and methods for restoring damaged bonds in hair, for example disulfide bonds, and protecting hair from the oxidative stress are disclosed in the present application. These formulations show the benefit of an improved and extended hair conditioning (thanks to the double bond on the cysteine groups). Specifically, the compositions provide a long-term hydration sensation and a smoothness sensation without leaving hair oily, an improved look (for example shine), an improved moisture resistance (tensile strength), an easiness of combing wet or dry hair, a reduced hair breaking, a reduced frizz, a reduced color fastness to washing and to UV radiations. The compositions according to the invention comprise one or more compounds able to interact with the keratin by means of a linking action due to the reaction with one or more thiol groups in the hair. The term "linking action" means the formation of a covalent, ionic or hydrogen, etc., bond. During the usual washing of hair, included shampooing and conditioning, the so formed covalent bonds are not sensitive to reduction or hydrolysis. The use of binding compositions prevents regression of the repaired bonds of hair to the previous free thiol group, after the application of the composition.

Improved methods for setting hair, for example curling, waving, straightening of permanent hair, are also disclosed. The binding compositions may be applied whenever necessary.

Traditional methods of permanent hair waving use hydrogen peroxide for re-establishing disulfide bonds after a reducing treatment. The process generally takes about three days to complete. The methods herein disclosed use one or more binding agent for hair repairing. In some embodiments of the present invention, the binding agent(s) and the free thiol groups form a covalent carbon-sulfur bond.

DETAILED DESCRIPTION OF THE INVENTION

I. Definitions

The term "hair" refers to one or more than one strand (also called "swatch") of hair, as well as the natural components of hair. Hair also refers to virgin hair or processed hair, for example hair that has been exposed to hair waving or hair straightening formulations.

"Pharmaceutically acceptable" and "cosmetically acceptable" are used interchangeably and refer to those compounds, materials, compositions and/or formulations, which are within the scope of scientific medical judgements, suitable for use in contact with the tissues of human beings and animals without excessive toxicity, irritation, allergic response, or other problems or complications commensurate with a reasonable benefit/risk ratio. More specifically, pharmaceutically acceptable refers to a material, compound, or formulation that is suitable for use in contact with the hair. Pharmaceutically acceptable materials are known to those of ordinary skill in the art.

"Shampoo", as used herein, generally refers to a liquid or semi-solid formulation applied to hair that contains detergent or soap for washing hair. "Conditioner", as used herein, generally refers to a formulation (e.g., liquid, cream, lotion, gel, semi-solid) applied to hair to soften hair, smooth hair, and/or change the hair sheen.

The terms "Linking agent" or "binding agent", as used herein, have the same meaning and refer to one molecule or two molecules able to form a covalent, ionic or hydrogen bond, with hair and generally require the formation of at least one covalent bond with the thiol group.

II. Binding Formulations

The formulations herein described relate to the treatment of hair. Said formulations comprise one or more binding agents, also called "active agents".

The binding agents can be combined in a linking (or binding) formulation with one or more carriers and/or pharmaceutically accepted excipients that are suitable and efficient when used on human hair and/or scalp and can be applied without undesirable collateral effects as irritation, itch, redness or similar adverse reactions.

The formulations can also contain an excipient that brings the pH to neutrality, or to a pH comprised in the range from about 3 to 12, preferably from 4 to 8.

The binding agent is usually present in a quantity from 0.05 wt. % to 30 wt. % of the formulation, preferably from about 2 wt. % to about 20 wt. % of the formulation.

The linking composition is stable in water solution for a period of at least from 2 to 12 months or longer and at a pH from 4 to 8 and at a temperature of about 25-30° C., preferably about 25° C.

The linking (or binding) composition of the present invention consists of one or more later defined chemical compounds having active functional groups able to react with thiol groups —SH to give a carbon-sulfur bond or, possibly, a sulfur-sulfur bond. The carbon-sulfur or the possible sulfur-sulfur bonds, so formed on the hair stem, are stable, for example to hydrolysis. The term "stable" means that the carbon-sulfur bonds or the sulfur-sulfur possible bonds formed on the hair stem remain intact for at least one week or more, when exposed to water at a pH from 4 to 8 and a temperature from about 10° C. to 50° C., preferably from 20° C. to 45° C., more preferably from 25° C. to 30° C. It is also preferable that the linking reaction to form the carbon-sulfur bond or the possible sulfur-sulfur bond takes place at room temperature, for example at from about 15° C. to about 35° C., preferably from about 22° C. to about 27° C.

Finally, the linking composition is soluble in water, and then it is preferably used as water solution.

The cosmetic composition of the present invention comprises an active part having a binding and antioxidant action, said active part being selected from the group consisting of:
(i) liposol maleate and
(ii) a mixture of liposol maleate and maleic acid, the ratio between them being from 5:95 to 95:5.

In a preferred embodiment of the present invention, the active part of the cosmetic formulation only consists of liposol maleate.

In another embodiment of the present invention, the active part consists of a mixture of liposol maleate and maleic acid, the weight ratio between liposol maleate and maleic acid being from 10:90 to 80:20.

In another embodiment of the present invention, the weight ratio between liposol maleate and maleic acid is 35:65.

In another embodiment of the present invention, the weight ratio between liposol maleate and maleic acid is 60:40.

Besides the active part, the cosmetic composition of the present invention may contain (from 0.05 to 90% by weight), other chemical compounds normally used in cosmetic formulations, one or more cosmetically acceptable excipients, wherein the one or more excipients are selected from the group consisting of water, surfactants, vitamins, natural extracts, preservatives, chelating agents, perfumes, antioxidants, hair coloring agents, proteins, amino acids, lubricants, emollients, penetrants, thickeners, viscosity modifiers, hair fixatives, film formers, emulsifiers, opacifying agents, propellants, vehicle agents, salts, pH adjusting agents, neutralizing agents, buffers, hair conditioning agents, anti-static agents, anti-frizz agents, anti-dandruff agents, and combination thereof.

Particularly:
a. Excipients

The formulations typically contain one or more cosmetically acceptable excipients. Cosmetically acceptable excipients include, but are not limited to water, preservatives, chelating agents, sunscreen agents, vitamins, hair coloring agents, proteins, antioxidants, amino acids, natural extracts such as plant extracts, humectants, emollients, fragrances, perfumes, oils, butters, penetrants, thickeners, penetrants, thickeners, viscosity modifiers, polymers, resins, hair fixatives, film formers, surfactants, detergents, emulsifiers, volatiles, opacifying agents, propellants, liquid vehicles, carriers, salts, pH adjusting agents (for example citric acid), neutralizing agents, buffers, hair conditioning agents, anti-static agents, anti-frizz agents, anti-dandruff agents, and combination thereof.

The formulations can contain at least two or more cosmetically acceptable excipients. In some forms, the formulations contain the binding agent, water and, optionally, a preservative and/or fragrance.

b. Surfactants

Surfactants are surface-active agents that are able to reduce the surface tension of water and cause the hair formation to slip across or onto the skin or hair. Surfactants also include detergents and soap. The surfactants may be amphoteric, anionic, or cationic. Suitable surfactants that may be used in the formulation include, but are not limited to, 3-aminopropane sulfonic acid, almond amide, almond amidopropyl betaine, almond amidopropylamine oxide, aluminum hydrogenated tallow glutamate, aluminum lanolate, aminoethyl sulfate, aminopropyl lauryl glutamine, ammonium C12-15 alkyl sulfate, ammonium C12-15 pareth sulfate, ammonium C12-16 alkyl sulfate, ammonium C9-C10 perfluoroalkylsulfonate, ammonium capryleth sulfate, ammonium capryleth-3 sulfate, ammonium monoglyceride sulfate, ammonium sulfate, ammonium isothionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol-30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearoyl gelatin/keratin amino acids/lysine hydroxypropyltrimonium chloride, amp-isostearoyl hydrolyzed collagen, apricot kernel oil PEG-6 esters, apricot amide, apricot amidopropyl betaine, arachideth-20, avocadamide, avocadamidopropyl betaine, babassuamide, babassuamidopropyl betaine, babassuamidopropylamine oxide, behenalkonium chloride, behenamide, behenamide, behenamidopropyl betaine, behenamine oxide, sodium laureth sulfate, sodium lauryl sulfate, a polyoxyether of lauryl alcohol or ceteareth-20, or combinations thereof. Suitable anionic surfactants include, but are not limited to, those containing carboxylate, sulfonate or sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

More than one surfactant may be included in the formulation.

The surfactants are optionally included in an amount ranging from about 0.01% to about 15% by weight of the formulation, preferably about 1% to about 10% by weight of the formulation.

c. Emollients

Emollient refers to a material that protects against wetness or irritation, softens, soothes, coats, lubricates, moisturizes, protects and/or cleanses hair. Suitable emollients for use in the formulations include, but are not limited to, a silicone compound (e.g., dimethicone, cyclomethicone, dimethicone copolyol or a mixture of cyclopentasiloxane and dimethicone/vinyldimethicone cross polymer, cyclopentasiloxane polysilicone), polyols such as sorbitol, glycerin, propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and fatty acid ester such as cetearyl isononanoate or cetyl palmitate. In a specific embodiment, the emollient is dimethicone, amidodimethicone, dimethiconol, cyclopentasiloxane, potassium dimethicone PEG-7 panthenyl phosphate, or combinations thereof.

More than one emollient may be included in the formulation.

The emollient is optionally included in an amount ranging from about 0.05% to about 10% by weight in the formulation, preferably from about 1% to about 5% by weight in the formulation.

d. Emulsifiers

The formulation may also contain one or more emulsifiers. Suitable emulsifiers include, but are not limited to, copolymers of an unsaturated ester and styrene sulfonate monomer, cetearyl alcohol, glyceryl ester, polyoxyethylene glycol ether of cetearyl alcohol, stearic acid, polysorbate-20, ceteareth-20, lecithin, glycol stearate, polysorbate-60, polysorbate-80, or combinations thereof. More than one emulsifier may be included in the formulation.

The emulsifier is optionally included in an amount ranging from about 0.05% to about 15% by weight of the formulation, preferably from about 0.1% to about 10% by weight of the formulation.

e. Preservatives

One or more preservative may be included in the formulation to prevent the microbial growth in the formulations. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediaminetetraacetic acid (EDTA), potassium sorbate, and/or grapefruit seed extract, or combinations thereof. More than one preservative may be included in the formulation. Other preservatives are known in the cosmetics industries and include salicylic acid, DMDM Hydantoin, Formaldeahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The preservative is optionally included in an amount ranging from about 0.01% to about 5% by weight of the formulation, preferably from about 0.3% to about 2% by weight of the formulation.

Preferably the formulation is avoided of paraben.

f. Conditioning Agents

One or more conditioning agents may be included in the formulation. Suitable conditioning agents include, but are not limited to, silicone-based agents (e.g., silicone quaternium-8), panthenol, hydrolyzed wheat and/or soy protein, amino acids (e.g. wheat amino acids), rice bran wax, meadowfoam seed oil, mango seed oil, grape seed oil, jojoba seed oil, sweet almond oil, hydroxyethyl behenamidopropyl dimonium chloride, aloe leaf extract, aloe barbadensis leaf juice, phytantriol, panthenol, retinyl palmitate, behentrimonium methosulfate, cyclopentasiloxane, quaternium-91, stearamidopropyl dimethylamine, and combinations thereof.

The conditioning agent/s is optionally included in an amount ranging from about 0.01% to about 5% by weight of the formulation, preferably from about 0.01% to about 3% by weight of the formulation.

g. Diluents

Diluent, as used herein, refers to a substance that dilutes the binding agent(s). Water is the preferred water. The formulation typically contains greater than 1% (by weight) water, preferably greater than 5% (by weight) water, more preferably greater than 50% (by weight) water, and most preferably greater than 80% (by weight) water. Alcohols, such as ethyl alcohol and isopropyl alcohol, may be used at low concentrations (about 0.5% by weight of the formulation) to enhance hair penetration and/or reduce odor.

h. Viscosity Modifying Agents

The formulations may contain one or more viscosity modifying agents, for example such as viscosity increasing agents. Classes of such agents include, but are not limited to, viscous liquids, particularly natural polymers. Said viscosity modifying agents are well known to people working in cosmetic.

i. Antioxidants

The formulation may contain one or more antioxidants. Examples include, but are not limited to, tocopheryls, BHT, ascorbic acid, *Camellia sinensis* leaf extract, ascorbyl palmitate, magnesium ascorbyl phosphate, carotenoids, resveratrol, triethyl citrate, arbutin, kojic acid, tetrahexydecyl ascorbate, superoxide dismutase, zinc, sodium metabisulfite, lycopene, ubiquinone, and combinations thereof.

l. Opacifying Agents

The formulation may contain one or more opacifying agents, sometimes used to make the formulations opaque.

Forms of the Formulations

The cosmetic composition of the present invention may be formulated in several different formulations.

m. Spray

The formulation may be in the form of a spray. The spray typically includes the binding agent(s) and a cosmetically acceptable carrier. In some embodiments, the carrier is water or a water and alcohol mixture. The spray formulation optionally includes an antioxidant, sunscreen agent, vitamin, protein, peptide, plant extract, humectant, oil, emollient, lubricant, thickener, hair conditioning agent, polymer, and/or surfactant. Preferably, the spray formulation includes a preservative. In some embodiments, the formulation includes a fragrance. In some embodiments, the formulation includes a surfactant. In some embodiments, the formulation contains water, fragrance, a preservative, and an active agent. In some embodiments, the formulation contains water, fragrance, a preservative, and a linking agent(s). In some embodiments, the formulation contains water, a preservative, fragrance, a linking agent(s), and an anti-static agent. In some embodiments, the formulation contains water, a preservative, fragrance, linking agent(s), and a hair conditioning agent. In some embodiments, the formulation contains water, a preservative, fragrance, a linking agent(s), and a surfactant.

The hair spray formulations may be dispensed from containers that include aerosol dispensers or pump spray dispensers. Such dispensers are known in the art and are commercially available from a variety of manufacturers.

When the hair spray formulation is dispensed from a pressurized aerosol container, a propellant may be used to force the formulation out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

The amount of propellant may range from about 10% to about 60% by weight of the formulation. The propellant may be separated from the hair repair formulation as in a two compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the formulation to the hair for a strengthening action.

n. Conditioner

The formulation may be in the form of a conditioner. The conditioner typically includes the linking agent(s) in a suitable carrier. Additionally, the conditioner may include cationic polymers derived from polysaccharides, for example cationic cellulose derivatives, cationic starch derivatives, cationic guar derivatives and cationic locust bean gum derivatives, synthetic cationic polymers, mixtures or combinations of these agents. The formulation may comprise other synthetic or natural polymers or polymers derived from biological preparation processes, which are functionalized, where appropriate, for example with cationic or neutral groups. These polymers may have a stabilizing or strengthening action on the formulation, and/or a conditioning action (deposition on the hair surface).

The linking active agent(s) may be included in any suitable concentration. Typical concentrations of the linking agent(s) in the conditioner range from small amounts such as approximately 0.01% (by wt), preferably at least 1% (by wt), to large amounts, such as up to 50% (by wt). Preferably the conditioner contains the linking agent(s) in a concentration ranging from 0.1% (by wt) to 5% (by wt), more preferably from 0.1% wt to 3% (by wt). Greater concentrations of binding agent(s) usually are not needed to achieve the desired results, but may be present in the conditioner.

o. Shampoo

The hair formulation of the present invention may be in the form of a shampoo. The shampoo typically includes the linking agent(s) in a suitable carrier. The linking agent(s) may be included in any suitable concentration. Typical concentrations of the linking agent(s) in the shampoo range from small amounts such as approximately 0.01% (by wt.), preferably at least 0.1% (by wt.), to large amounts, such as up to 50% (by wt.). Preferably the shampoo contains the linking agent(s) in a concentration ranging from 0.1% (by wt) to 3% (wt). While greater concentrations of linking agent(s) could be present in the shampoo, they are generally not needed to achieve the desired results, but may be present in the shampoo.

Additionally, the shampoo may include from about 0.5% to about 20% by weight of a surfactant material. Surfactants utilized in shampoo compositions are well-known in the art and are disclosed, for example, in U.S. Pat. No. 6,706,258 to Gallagher et al. and U.S. Pat. No. 7,598,213 to Geary et al.

p. Cream

The hair formulation of the present invention can be in the form of a cream. The cream typically includes the linking agent(s) in a suitable carrier. The linking agent(s) may be included in any suitable concentration. Typical concentrations of the linking agent(s) in the cream, range from small amounts such as approximately 0.01% (by wt), preferably at least 0.1% (by wt), to large amounts, such as up to 50% (by wt). Preferably the cream contains the binding agent(s) in a concentration ranging from 0.1% (by wt) to 5% (by wt), more preferably from 0.1% (by wt) to 3% (by wt). While greater concentrations of agent(s) could be present in the cream, they are generally not needed to achieve the desired results, but may be present in the cream.

Additionally, the cream may include oil, a hair conditioning agent, and/or a thickening agent. The cream may also include a fragrance, a plant extract, and/or a surfactant. The cream may be packaged in a tube, tub, bottle, or other suitable container.

q. Liquid Binding Agent(s) Formulation

In some embodiments, a liquid linking agent formulation is provided, which is mixed at the time of use with a second formulation, such as a coloring or highlighting formulation. In these embodiments, the liquid linking agent formulation may contain any suitable concentration of binding agent(s) in a suitable carrier, typically a diluent, such as described above. The concentration of the binding agent(s) is suitable to provide a mixture with the appropriate final volume and final concentration of linking agent(s).

For example, a liquid linking agent formulation can contain a concentration of linking agent(s) ranging from about 0.05% (by wt) to about 30% (by wt) or greater. In a preferred embodiment, the liquid linking agent formulation contains about 20% (by wt) linking agent(s).

The terms "highlighting" and "bleaching" are herein used are the same meaning.

For highlighting applications, prior to use, a sufficient volume of a binding formulation is mixed with a sufficient volume of a highlighting formulation to form a highlighting mixture having the desired concentration of linking agent(s). Typical concentrations of the linking agent(s) in the highlighting mixture range from small amounts, such as approximately at least 0.01% (by wt), preferably at least 0.1% (by wt), to large amounts, such as up to 50% (by wt). Preferably the highlighting mixture contains the linking agent(s) in a concentration ranging from 0.1% (by wt) to 5% (by wt), more preferably from 0.1% (by wt) to 3% (wt). While greater concentrations of linking agent(s) could be present in the highlighting mixture, they are generally not needed to achieve the desired results.

Alternatively, two separate formulations are applied, as a first formulation containing a bleaching agent (that is the highlighting formulation), and a second formulation containing a binding agent(s) (that is the linking formulation) in an amount suitable to covalently bind the free thiol groups. The bleaching formulation producing free thiol groups in hair can be applied as first. Afterwards, the linking formulations able to bind the free thiol groups can be applied.

r. Powder

In some embodiments, a powder formulation consisting of linking agent(s) in an anhydrous form, mixed with suitable percentages of ammonium persulfate, sodium and potassium persulfate powders, anti-aggregation and flowing agents as silica, pH modifiers as sodium metasilicate, sodium and magnesium carbonate, is provided.

Application of the Formulation

The present invention provides a method for treating hair comprising:

(a) applying to hair a cosmetic formulation comprising an active part having a binding and antioxidant action, wherein said active part is selected from the group consisting of:

(i) liposol maleate and (ii) a mixture of liposol maleate and maleic acid, the weight ratio between them being from 5:95 to 95:5.

In an embodiment of the present invention, the active part (or binding agent(s) or linking agent(s)) of the cosmetic composition only consists of liposol maleate.

In another embodiment of the present invention the active part consists of a mixture of liposol maleate and maleic acid, the weight ratio between them being from 10:90 to 80:20.

In another embodiment of the present invention, the weight ratio between liposol maleate and maleic acid is 35:65.

In still another embodiment of the present invention, the weight ratio between liposol maleate and maleic acid is 60:40.

Both maleic acid and the mixture maleic acid+liposol maleate are water soluble. In relation to maleic acid+liposol maleate mixtures, they can be prepared starting from the single compounds that are mixed and subsequently dilute with water, or starting from the properly mixed single water solutions.

In the preferred embodiment of the present invention, the binding composition of the present invention is a water solution.

As an alternative, in the particular case of a bleaching treatment, a powder solid formulation can be used, said formulation comprising:

1) a binding agent(s), wherein the solid binding agent is selected from the group consisting of:

1a) liposol maleate powder and 1b) a mixture of liposol maleate and maleic acid, both as powder, the ratio between them in said mixture being from 5:95 to 95:5, preferably from 10:90 to 15:85, preferably 35:65 and 60:40, 2) powder solid ammonium, sodium and potassium persulfate in a quantity from 1 to 50%, useful for hair bleaching.

The above disclosed bleaching formulation can further comprise solid components:

3) anti-aggregating and flowing agents, as silica, kaolin and magnesium oxide in an amount between 1 and 10%, pH adjusting agents as sodium meta silicate, sodium and magnesium carbonate.

The above disclosed bleaching or decoloring formulation is used in the hair decoloring process, said process comprising:

(a) mixing the solid powder formulation with a solution or an emulsion of hydrogen peroxide, (b) optionally adding a binding part to the mixture obtained in step (a), (c) applying to hair the mixture of step (b).

Maleic acid (or cis-butendioic acid) is a well-known unsaturated dicarbossilic acid having the general formula $C_4H_4O_4$.

As liposol maleate, (CAS No: 865661-00-3, $C_{16}H_{28}N_2O_2S_2$—Molecular weight 392.5), it is an amine named 1,2-dithioane-3-pentanamide, N-(2-dimethylamino) ethyl salified with a mole of maleic acid.

As known to people skilled in this area, both the compounds maleic acid and liposol maleate, that are the active part of the present invention, can get bound to free thiol groups (let say—SH groups) giving a carbon-sulfur bond, and in case sulfur-sulfur bond.

The above described methods of the present invention relate to a conditioning and antioxidant treatment of damaged hair in which thiol groups are present.

A. Treatment of Damaged Hair Having Free Thiol Groups.

Before treatment with the cosmetic composition of the present invention, hair is damaged and presents free thiol groups. The binding composition of the present invention is applied on hair in order to bind the free thiol groups. Preferably, the linking composition is applied at least within a week following damage of hair, preferably within three days, more preferable the same day.

A1) Rinsing or Washing Hair

Optionally, hair may be washed with a shampoo and/or a conditioner before applying the linking composition of the present invention. Alternatively, hair can be only rinsed with water.

A2) Applying the Linking Formulation on Hair

After washing with shampoo, conditioning and/or rinsing, the formulation is applied on hair, preferably on dry hair. This application step can be repeated from 1 minute to 180 minutes in relation to the type of application, after the first application of the formulation.

The linking (binding) formulations of the present invention may be used as a daily hair conditioning and antioxidant treatment. Usually, the formulation is applied in an amount sufficient to saturate hair.

The linking composition may be applied on hair as a single application, or the application of the linking composition may be repeated one or more times. Typically, the amount of linking composition applied in each application is sufficient to saturate hair. The volume of linking composition formulation applied to hair in each application may be about 1 to 100 ml per person, depending on their length and volume of hair.

A3) Removing the Linking Composition

In the preferred embodiment of the present invention, hair is washed and rinsed after final application of the linking composition. Preferably hair may be rinsed and washed about 30 minutes after the application, preferably within 10 seconds to 60 minutes following application depending on type of hair. The linking agent(s) covalently binds free thiol groups of hair. The thiols remain bound for at least one weak or more, since the carbon-sulfur bonds are strong.

B. Chemical Treatment of Hair with a Reducing Agent.

In one embodiment, prior to treatment with the binding composition, hair has been subjected to a reducing agent used for waving, curling and/or straightening.

B1. Apply a Reducing Agent on Hair.

The first step in waving, straightening, or curling hair is breaking the cysteine disulfide bonds to form free thiol moieties. The process for breaking the cysteine disulfide bonds is via application of a reducing agent. The process for applying the reducing agent involves following normal perming or hair straightening procedures that are known to those skilled in the art. For example, to perm hair, hair is firstly washed and set on perm rods of various sizes. Second, a reducing agent, such as thioglycolate reducing solution or lotion is applied to hair. Hair is allowed to set for a specified period of time, and then the thioglycolate solution is rinsed from hair.

The application of hydrogen peroxide in this process is optional. In some processes, such as when treating previously chemically treated hair, hydrogen peroxide is generally not used. In other processes, such as when perming virgin hair, hydrogen peroxide may be added. In these embodiments, hydrogen peroxide is typically added after the reducing agent is rinsed out. Then the hydrogen peroxide is rinsed from hair prior to adding the binding agent(s).

B2. Apply the Binding Agent(s)

Subsequent to the reducing treatment, one or more binding agent, or a formulation thereof is applied to hair. Although the agent(s) is typically applied on the same day as treatment with the reducing agent, it may be applied later such as within 1 to 2 weeks following treatment with the reducing agent.

Typically, the amount of linking agent(s) formulation applied is sufficient to saturate hair. The linking composition is generally rinsed and shampooed from hair after the desired level of hair waving, straightening, or curling is achieved. In some embodiments, the binding agent(s) is rinsed from hair immediately following the final application of the binding agent(s). Alternatively hair may be rinsed and washed within about 30 minutes following application, preferably between about 5 minutes and about 20 minutes after the final application of the linking agent(s) to hair, depending on the hair type. The linking agent(s) can be rinsed from hair within few seconds after application, and still achieve a desired level of hair waving, straightening or curling.

The linking agent(s) may be applied to hair as a single application, or application of the linking agent(s) may be repeated one or more times. Typically, the amount of linking formulation applied in each application is sufficient to saturate hair. In some embodiments, application of the linking agent(s) could be repeated immediately after the first application. In some embodiments, the second application is about 7 minutes after the first application.

The linking agent(s) is rinsed from hair after its application. Hair may be rinsed and washed immediately after final application of the linking agent(s). Alternatively, hair may be rinsed and washed some minutes after the final application of the linking agent(s), such as about 15 minutes to about 30 minutes, preferably about 20 minutes after the repeated application of the linking agent(s) to hair.

The linking agent(s) covalently bonds free thiol groups on hair. Thiol groups remain bound for at least one week or more.

In contrast, traditional perms which use only hydrogen peroxide are generally not washed for 48 hours following application (washing hair prior to 48 hours following a traditional permanent may result in significant loss in the amount of curl in hair and/or causes damages to hair).

The compositions described herein improve the hair quality such as appearance (e.g. shine) and feel and increase wet strength (for example tensile strength), and improve the oxidation stability (resistance to UV radiations), reduce the hair breakages when hair is submitted to subsequent treatments, as coloring.

In case of colored hair, treatment with the linking agent(s) according to the present invention enables to maintain coloration for a more extended period of time in relation both to washing and UV radiations exposition.

B3. Apply the Coloring Formulation to Hair

The coloring formulation is generally applied to an individual's hair following normal hair coloring procedures that are known to those skilled in the art. Typically, hair color treatments include two complementary processes: applying a bleaching formulation to bleach the hair's natural pigment and/or other artificial pigments present in the hair, and diffusion of dye precursors into the hair, followed by coupling reactions that result in the formation of chromophores within the hair shaft, which are too large to diffuse out of hair. The bleaching formulation typically contains a bleaching agent to lighten hair and produce free thiol groups. The hair coloring formulation may be a highlighting formulation, such as formed by mixing bleach powder and developer. More complex colors may contain several precursors and many couplers, and may involve multiple reactions.

The dye precursors may contain several ingredients, each with different functions. The first ingredient is usually an alkalizing agent (usually ammonia and/or an ammonia substitute, such as monoethanolamine [MEA]). The alkalizing agent serves a number of roles in the hair colorant process including swelling the hair fiber to aid in diffusion of the dye precursors. The dye precursors generally include p-diamines and p-aminophenols. Precursors are oxidized to active intermediates once they have penetrated the hair shaft. Intermediates then react with color couplers to create wash resistant dyes. More specifically, the intermediates, in the presence of an oxidant, couple with another oxidation dye intermediate molecule to form a large fused ring color compound within the hair shaft. The precursor intermediate should penetrate the hair shaft prior to the coupling reaction since the fused ring product is too large to penetrate the hair shaft. Couplers modify the color produced by the oxidation of precursor compounds. The primary difference between demi-permanent and permanent products is the alkalizing agent and the concentration of peroxide. The cuticle does not swell as greatly with demi-permanent dyes, making dye penetration less efficient compared to permanent coloring products.

The hair dying process may be followed by a shampoo and conditioning treatment, a neutralizing rinse or an acid balanced shampoo containing in addition to cationic or amphoteric surfactants, cation-active emollients and quaternary polymers. Alternately, the hair dying process may be followed by application of the linking agent formulations described herein, before a shampoo and/or conditioning treatment.

B4. Apply the Linking Formulation

The linking formulation may be applied simultaneously with the hair coloring formulation or subsequently to the application of the hair coloring formulation. For example, the linking formulation may be mixed with the hair coloring treatment and the mixture, containing both the linking agents and the hair coloring treatment, may be applied to hair.

Alternatively, subsequent to coloring hair, the linking formulation is applied to hair. Although the linking agent(s) is typically applied on the same day as the coloring treatment, it may be applied later such as within 1 to 2 weeks following treatment with the colouring treatment. Typically, the amount of linking formulation (or a mixture of the linking formulation and the hair coloring formulation) applied is sufficient to saturate the hair. The linking agent(s) may be applied to hair as a single application, or application of the linking agent(s) may be repeated one or more times. Typically, the amount of linking agent formulation applied in each application is sufficient to saturate the hair. The volume of linking formulation applied to hair in each application may be about 1 to about 100 mL per person depending on their length and volume of hair. In some embodiments, application of the linking agent(s) could be repeated immediately (for example between 10 to 15 second) or approximately after the first application.

The linking agent(s) can be rinsed or shampooed from hair immediately following application or alternatively some minutes after application. Alternatively, the linking agent(s) may be rinsed from hair within about 30 minutes following application, preferably between about 5 to 20 minutes, more preferably about 10 minutes after application of the linking agent(s) to hair, depending on hair type.

If the linking formulation is combined with the hair coloring treatment and applied as a mixture to hair, then the mixture remains on hair as long as needed for the hair coloring treatment. Typically the mixture is applied for approximately 10-40 minutes. The mixture is removed from hair in accordance with standard methods for hair coloring treatments, e.g., rinse and shampoo, approximately 10 minutes after applying the mixture.

The linking formulation is rinsed from hair after its application. The hair may be rinsed and subsequently washed immediately (e.g. within 10 to 15 seconds following application) after the final application of the linking agent(s). Preferably, hair is rinsed and/or washed about 10 minutes or later after the final application of the linking agent(s), such as about 15 minutes to about 30 minutes, optionally about 20 minutes after repeated applications of the linking agent(s) to hair.

The linking agent covalently binds the free thiol groups on hair. Thiols remain bound for at least one week or more.

The formulations described herein improve hair quality, such as appearance (e.g. shine) and feel, and decreases the hair breakage when hair is subjected to subsequent chemical treatments. Particularly, the presence of the linking agent(s) having antioxidant properties enables to preserve the structure of hair and the coloration from damages due to photo-oxidation and to free radicals.

The following experimental part will show that the linking formulations of the present invention allow to protect hair from oxidative and photo-oxidative damages, in a definitely superior level in comparison with the prior art formulations, also after repeated washing treatments.

Particularly, one composition of the present invention consisting of liposol maleate and maleic acid is more efficient than the single components, let say liposol maleate alone and maleic acid alone. This feature shows a synergic effect between the two components, said effect being totally unexpected.

The following examples are reported for a better understanding of the present invention.

EXAMPLE 1

Color Fastness to Washing

Six hair samples from a human subject, level 7 standard weight and length, are colored with the coloring formulation Davines Mask with Vibrachrom 6.35.

The coloring formulation was applied along with the Davines Activator 20 vol., hydrogen peroxide emulsion, according to Davines operating manual, in a 1:1.5 ratio.

The coloring formulation was applied in a quantity sufficient to color all the fibers of the swatches, then wrapped in an aluminum foil and left on for 35 minutes.

Afterwards, the swatches were rinsed with Davines SOLU shampoo of the Essential Hair Care line, directly on the previously wet swatches and rinsed for 30 seconds in order to remove the mixture.

Then, swatches are treated as follows:

5 g of 2% maleic acid water solution, 5 g of 2% liposol maleate (Sabinsa Corporation) water solution, 5 g of 2% of On Protection (7% Liposol maleate and 13% maleic acid) water solution 5 g of 2% of On Protection (12% Liposol maleate and 8% maleic acid) water solution, 5 g of 2% Olaplex® Bond Multiplier No 1 water solution.

A non-treated swatch is used as reference.

The specific treatments are left on hair fora period of 10 minutes at room temperature.

After 10 minutes, the swatches are rinsed 5 times with a Sodium Laureth-2 Sulfate (Zetesol Les 2/SL®) solution to pH 7.5. The rinsing procedure consists on providing 1.5 g of the surfactant solution per swatch, putting it on the swatch, and massaging for 10 seconds, then rinsing.

The rinsing treatment is carried out dipping the individual swatch for 10 times in a beaker containing 100 g water, in order to collect the rinsing water.

Then, the different rinsing waters were evaluated (see FIG. 1).

Conclusion:

The rinsing water from the swatch treated with the On Protection composition containing 12% Liposol maleate and 8% maleic acid, is clearly more limpid in comparison with the other solutions. At the second rank is the rinsing water in the presence of On Protection containing 7% Liposol maleate and 13% maleic acid, then (third) the rinsing water using Liposol maleate 2%, fourth rinsing water using 2% Olaplex® Bond Multiplier No 1. Rinsing water using maleic acid 2% is comparable (in relation to color intensity), to the non-treated swatch (fifth and sixth).

EXAMPLE 2

Color Fastness to UV Radiations After Washing With an Alkaline Shampoo

Five hair samples from a human subject, level 5, standard weight and width, were treated with the bleaching powder Davines Mask Hair Bleaching Powder mixed with an activator, hydrogen peroxide emulsion Davines Activator 40% vol. in a 1:2 ratio.

The samples, wrapped in an aluminum foil, were left on for a period of 50 minutes at room temperature. The hair samples were subsequently washed with DEDE Davines Shampoo of the line Essential Hair Care, dried and treated with the coloring formulation Davines Mask With Vibrachrom 6.22. The color was applied as a mixture with the Davines Activator 20 vol., the ratio activator: color being 1.1.5, as disclosed in the Davines Operating Manual. The mixture was left on for a period of 35 minutes at room temperature. Afterwards, the hair samples were carefully rinsed with DEDE Davines Shampoo of the line Essential Hair Care and dried using an airdryer. The above five samples are treated using:

1) 5 g of 2% liposol maleate (Sabinsa Corporation) water solution,
2) 5 g of 2% maleic acid water solution,
3) 5 g of 2% Olaplex® Bond Multiplier No 1 water solution
4) 5 g of 2% of On Protection (7% Liposol maleate and 13% maleic acid) water solution.

The samples were left for a period of 10 minutes.

After the left on period, the swatches were carefully rinsed with water.

Then the swatches were carefully rinsed with a Sodium Laureth-2 Sulfate (Zetesol Les 2/SL®) solution to pH 7.5. The rinsing procedure consists on providing 1.5 g of the surfactant solution per swatch, putting it directly on the swatch, massaging for 10 seconds, and rinsing 10 times in a beaker containing 100 g water.

After the rinsing treatments the hair samples were carefully washed, dried with an airdryer and exposed to the Sun test (Q-Lab Q-sun Xenon Test Chamber-Model XE-1); test conditions: 70 TUV, 45° C., 10H.

Results:

By a visual analysis made by expert people, the following remarks can be made:

as above described, the bleached and subsequently colored swatches show that the treatment with "On protection" better protects from discoloring due to UV radiations after several washings, maintaining the color more intense and vibrant in comparison with the swatches treated with Liposol maleate, Olaplex® Bond Multiplier No 1 and maleic acid.

Photos relating to the swatches before and after these treatments are available at Davines Research and Development Laboratories.

EXAMPLE 3

Color Fastness to UV Radiations

Five level 5 swatches, weight and width standard, were discolored using the bleaching powder Davines Mask Hair bleaching Powder mixed with an activator, hydrogen peroxide emulsion, Davines Activator 40 vol. in a ratio 1:2, according to Davines Operation Manual. Swatches were left on for 50 minutes at room temperature wrapped in an aluminum foil.

At the end of this period, the swatches were washed with DEDE Davines Shampoo of the Essential Hair Care line, dried and treated with the coloring formulation Davines Mask With Vibrachrom 6.22. The color was applied along with the activator Davines Activator 20 vol, in a ratio 1:1.5 according to Davines Operation Manual. The mixture was allowed to stand at room temperature for a period of 35 minutes. After that, the swatches were carefully washed with a 15% solution of Sodium laureth-2 sulfate (Zetesol Les2/SL®) at a pH of 7.5, massaged for 10 seconds and rinsed for 30 seconds with cold running water. This treatment was repeated two times, and the swatches were carefully dried.

Then, the swatches were treated as follows:

5 g of 4% liposol maleate (Sabinsa Corporation) water solution 5 g of 2% liposol maleate (Sabinsa Corporation) water solution 5 g of 2% maleic acid water solution 5 g of 2% Olaplex® Bond Multiplier No 1 water solution 5 g of 2% of On Protection (7% Liposol maleate and 13% maleic acid) water solution.

Every protective treatment was left on fore period of 10 minutes at room temperature. After that, they were rinsed with cold running water and dried with an airdryer.

Finally, the swatches were exposed to the Sun test (Q-Lab Q-sun Xenon Test Chamber-Model XE-1); test conditions: 70 TUV, 45° C., 10H.

Results:

The evaluations were made after UV radiations treatment.

The visual inspection made by skilled technicians gave these results:

The swatch treated with On Protection (7% liposol maleate and 13% maleic acid) is more intensive in coloration, displaying, after the UV treatment, a greater capability in color retention, in relation to both intensity and reflection.

The swatches treated with liposol maleate 2% and with liposol maleate 4% have similar color retention after UV treatments, but lower than On Protection, i.e. the combination of liposol maleate and maleic acid. The swatches treated with Olaplex® Bond Multiplier No 1 are the less efficient as to color retention after UV radiations.

Photos relating to the swatches before and after these treatments are available at Davines Research and Development Laboratories.

EXAMPLE 4

Protection of Hair From Bleaching Treatment

Six level 7 swatches of hair, weight and width standard, had been discolored using the bleaching powder Davines Mask Hair bleaching Powder mixed with an activator, hydrogen peroxide emulsion, Davines Activator 40 vol. in a ratio 1:2, according to Davines Operation Manual. The following specific compositions were separately added to the mixture:

a) 3.5 g of a 12% Liposol maleate (Sabinsa Corporation) water solution;

b) 3.5 g of a 12% On Protection (7% Liposol maleate and 13% maleic) water solution;

c) 3.5 g of a 12% of On Protection (12% Liposol maleate and 8% maleic acid) water solution;

d) 3.5 g of a 12% maleic acid water solution;

e) 3.5 g of a 12% Olaplex® Bond Multiplier No 1 water solution;

f) a swatch without active components (as reference).

The swatches were left on for 30 minutes at room temperature wrapped in an aluminum foil.

After that, the swatches were rinsed using cold running water and carefully washed using Davines SOLU shampoo of the Essential Hair Care line.

The above described treatment is repeated a second time, exactly according to the previous treatment, in order to better appreciate the differences in the hair appearance.

After the left on period, the swatches were rinsed using cold running water for removing the mixture and further treated with Davines SOLU shampoo of the Essential Hair Care line.

Then, 2.5 g of the conditioner MOMO of the Essential Hair Care line are applied; left on for one minute and subsequently rinsed using cold running water.

Finally, the swatches were towel dried, dried with an airdryer and combed using a fine-tooth comb.

Results:

According to a first sensorial analysis made by skilled people, already during the drying process these remarks may be made: the swatch treated with a 12% On Protection solution containing 12% liposol maleate and 8% maleic acid results ameliorative in comparison with the swatches treated with Olaplex® 12% water solution, regarding silkiness, smoothness and compactness of the swatches. This result becomes more marked after drying: the final part of the swatch treated with a 12% On Protection water solution, containing 12% liposol maleate and 8% maleic acid, remains more compact, soft, silky, more shining and easier to comb.

As the swatch treated with a 12% water solution of Olaplex® Bond Multiplier No 1, the swatch treated with a Liposol maleate 12% solution is better in relation to compactness, silkiness and smoothness.

As the ranking of the other mixtures, the followings are: swatch treated with a 12% water solution of Olaplex® Bond Multiplier No 1, swatch treated with a 12% maleic acid water solution and finally the reference swatch (no treatment, mixture containing only powder+activator).

EXAMPLE 5

Hair Resistance to Bleaching Treatment

Five swatches of hair, weight and length standard, level 5, are treated with the coloration Davines Mask With Vibrachrom 4.0 mixed with the activator Davines Activator 20 vol., emulsion containing hydrogen peroxide, in a ratio of 1:1.5 as disclosed in the Davines manual and left on at room temperature for 35 minutes in a ratio of 1:1.5 as disclosed in the Davines manual.

During the left on period, the swatches were wrapped up in tinfoil and left at room temperature. After that, the swatches were rinsed with abundant running water and then washed with the Essential Hair Care SOLU shampoo of Davines line, washed and carefully dried with an airdryer.

At the end of the coloring process, the bleaching treatment starts.

Every swatch is decolored with 20 g of the bleaching powder Davines Mask Hair Bleaching Powder mixed with 40 g Davines Activator 40 vol.

Before application on the swatches, the mixtures are singularly added with the following solutions:

9 g maleic acid—20% water solution 9 g Liposol maleate (Sabinsa Corporation)—20% water solution, 9 g Olaplex® Bond Multiplier No 1, 9 g On Protection (13% maleic acid and 7% Liposol maleate)

During the bleaching process, all the swatches are wrapped up in tinfoil, and left on for 50 minutes at room temperature.

After the left on period, the swatches are shampooed using Davines Hair Care DEDE shampoo and combed using a large-tooth comb.

A tensile strength test was carried out on all single swatches. The tests were made using a dynamometer Texture Analysis Plus (Extended Height) using pneumatic clamps.

The studied parameter is the Tensile Strength, let say the force of traction necessary to break hair. The results were compared with the data of a non-decolored swatch, virgin swatch. Five measurements for each hair 6 cm long, and at constant rate of 0.5 mm/sec., were made. Here below the results are reported:

| Sample | Tensile Strength N |
| --- | --- |
| No treatment | 1.14 ± 0.11 |
| Bleaching with maleic acid | 0.69 ± 0.07 |
| Bleaching with liposol maleate | 0.98 ± 0.11 |
| Bleaching with Olaplex ® Bond Multiplier No 1 | 0.97 ± 0.1 |
| Bleaching with On Protection | 1.24 ± 0.07 |

Results:

By comparison of the N (Newton) values, the protective linking agent(s) On Protection gives to hair a greater resistance to breakage (i.e. the force necessary to break hair is higher in the case of On Protection). Moreover the On Protection treatment is able to restore the original strength of hair, corresponding to the non-treated virgin swatch.

EXAMPLE 6

Protection of Hair Against Repeated Bleaching Treatments

Five swatches of hair, weight and length standard, level 5, are treated with the coloration Davines Mask With Vibrachrom 4.0 mixed with the activator Davines Activator 20 vol., emulsion containing hydrogen peroxide, in a ratio of 1:1.5 as disclosed in the Davines manual and left on at room temperature for 35 minutes.

After that, the swatches are rinsed with abundant running water, and then washed with Davines Hair Care SOLU shampoo, again rinsed, and dried.

At the end of the coloring treatment, the decoloring treatment starts.

The swatches are bleached with 20 g bleaching powder Davines Mask Bleaching Powder mixed with 40 g activator Davines Activator 40 vol, said mixture being subsequently added with:

9 g Maleic Acid in 20% water solution,
9 g Liposol maleate (Sabinsa Corporation) in 20% water solution,
9 g Olaplex® Bond Multiplier No,
9 g On Protection (8% maleic acid and 12% Liposol maleate),
a mixture without protective agents: reference swatch.

During the decoloring process, all the swatches are wrapped up in tinfoil and left on at room temperature for 50 minutes.

At the end of the left on period, all the swatches are washed with Davines Hair Care DEDE shampoo and combed using a large-tooth comb.

This process is repeated from 5 to 7 times to destructure the swatches with repeated bleaching processes in order to highlight the degree of hair protection from different protective agents.

The sensorial evaluation of the swatches shows that the swatch treated with a solution of On Protection is more compact, soft, healthy and shiny, comparing with the other swatches treated in a different way.

Moreover, the quality of the hair structure of bleached hair was evaluated using a micro camera Aramol Professional Microscope APM-200. This analysis is consistent with the previously described sensorial evaluation. Really, the analysis with the micro camera of the swatch treated with On Protection (8% maleic acid and 12% liposol maleate) shows an image characterized by more closed cuticles and a more compact and smooth structure in comparison with the images of hair treated using different solutions. Also by using the micro camera images, the linking agent composition On Protection (8% maleic acid and 12% liposol maleate) gives a better result in relation to the hair structure protection.

After the sensorial and micro camera evaluation, the single swatches are submitted to the following treatment.

Every swatch is treated with 2.5 g of the conditioner Davines OI CONDITIONER to which the following treatment is added:

5% maleic acid,
5% liposol maleate (Sabinsa Corporation),
5% Olaplex® Bond Multiplier No 1,
5% On Protection (8% maleic acid and 12% liposol maleate.

The reference swatch is treated only with 2.5 g of the conditioner Davines OI CONDITIONER.

The so prepared mixture is applied to the single swatches, homogeneously layered and left on for 5 minutes and subsequently rinsed with running water for 1 minute.

Then, the swatches are towel dried, dried using an airdryer and combed with a large-tooth paddle brush during drying (12 brushes for each swatch).

Then, the combability tests are made.

Combability Test

The combability test was carried out using a Texture Analysis Plus (Extended Height) using a comb with tooth on four lines.

FIG. 2 is a graph showing the force exerted by the brush for combing 6 times the swatch.

The graph shows that the force necessary to comb the swatch treated with On Protection is lower (except the second combing) than all the other swatches treated with different compositions.

Conclusions:

The swatch repeatedly treated with the protective agent On Protection (12% liposol maleate and 8% maleic acid) according to the invention is more compact, has a healthy look and is smoother in comparison with the swatches differently treated as above described, or to the non-treated (reference) swatch.

Moreover, after the conditioning treatment the swatch treated with On Protection containing 12% liposol maleate and 8% maleic acid is also more easily combed.

EXAMPLE 7

Hair Fastness and Easy Bleaching

Four swatches of human hair, weight and length level 5, are used.

Bleaching Treatment.

The swatches are bleached using a mixture of 20 g Davines Mask Hair Bleaching Powder and 40 g Davines Activator 20 vol. to which the following compounds are added:

a) 3.5 g 12% maleic acid in water,
b) 3.5 g 12% Liposol maleate (Sabinsa Corp.) in water,
c) 3.5 g 12% Olaplex® Bond Multiplier No 1 in water,
d) 3.5 g 12% On Protection (12% Liposol maleate+8% maleic acid) in water.

During the bleaching process, all the swatches are wrapped up in aluminum foil, and afterward they are left on for 120 minutes at room temperature.

After the left on period, every swatch is rinsed with abundant running water and washed with a Sodium Lauth-2 sulfate (Zetesol Les 2/SL®) 15% water solution and to a pH 7.5, and dried by combing with a large-tooth comb.

The swatches are subsequently washed until a complete removal of the product.

Tests carried out:
1. Tensile strength
2. Qualitative evaluation of swatches
1. Tensile Strength The Tensile Strength Test was made with a dynamometer Texture Analysis Plus (Extended Height) using pneumatic clamps.

The tensile strength of hair treated with different compositions was compared with the tensile strength of the non-bleached virgin swatch (positive reference) and the tensile strength of the swatch treated only with Davines Mask Hair Bleaching Powder without a protective agent (negative reference). Five measurements for each single 6 cm long hair, and at constant rate of 0.5 mm/sec., were made. Here below the results are reported:

| Sample | Tensile Strength N |
| --- | --- |
| No treatment | 0.83 ± 0.06 |
| Virgin swatch | 1.14 ± 1.11 |
| Bleaching with maleic acid | 0.83 ± 0.05 |
| Bleaching with liposol maleate | 1.06 ± 0.13 |
| Bleaching with Olaplex ® Bond Multiplier No 1 | 0.81 ± 0.07 |
| Bleaching with On Protection | 0.99 ± 011 |

Conclusion:

The protective compositions On Protection (containing 12% Liposol maleate+and 8% maleic acid) and Liposol Maleate alone, clearly show an improvement, in comparison to other treatments, in the resistance to hair breakage, since the force necessary to break hair is greater when using On Protection (containing 12% Liposol maleate and 8% maleic acid) and Liposol Maleate alone.

2. Qualitative Evaluation

A further qualitative evaluation of the swatches was made, both as bleaching level and as conditioning effect in comparison with the negative reference (only bleaching).

Conclusion:

The bleaching level of the swatches treated as above, had been evaluated by a person skilled in this field as not different in a significant way, but worse of the swatch bleached only with bleaching powder.

Immediately after the treatments, the swatch treated with On Protection (12% Liposol maleate and 8% maleic acid) is more conditioned than the swatches treated with different agents.

EXAMPLE 8

A Reducing Treatment: Curl Resistance to Repeated Washings

Five level 5 swatches natural hair, weight and width standard, had been washed with Davines DEDE shampoo of the Essential Hair Care line.

Then they had been towel dried, rolled on curlers 1 cm diameter and treated with a reducing agent as below described:

1) 100 ml Davines Balance Curling System #1,
2) 100 ml Davines Balance Curling System #1 added with 1.8 ml of a 20% maleic acid solution,
3) 100 ml Davines Balance Curling System #1 added with 1.8 ml of a Liposol maleate 20% solution (Sabinsa Corporation),
4) 100 ml Davines Balance Curling System #1 added with 1.8 ml of Olaplex® Bond Multiplier No 1,
5) 100 ml Davines Balance Curling System #1 added with 1.8 ml of On Protection (7% liposol maleate and 13% maleic acid).

The above described reducing formulations (2 ml per hair swatch) were applied and left on for 30 minutes.

After the left on period, the swatches were washed with hot running water for one minute and left 10 minutes towel dried on air without any treatment, in order to stabilize the treatment.

Five neutralizing solutions are prepared:

1) 100 ml neutralizing solution Davines Bouclè Biowaving System Extra Delicate Neutralizer hydrogen peroxide 2.1%,
2) 100 ml neutralizing solution Davines Bouclè Biowaving System Extra Delicate Neutralizer added with 1.8 ml of maleic acid 20% water solution,
3) 100 ml neutralizing solution Davines Bouclè Biowaving System Extra Delicate Neutralizer added with 1.8 ml of Liposol Maleate 20% water solution (Sabinsa Corporation),
4) 100 ml neutralizing solution Davines Bouclè Biowaving System Extra Delicate Neutralizer added with 1.8 ml Olaplex® Bond Multiplier No 1,
5) 100 ml neutralizing solution Davines Bouclè Biowaving System Extra Delicate Neutralizer added with 1.8 ml On Protection (7% liposol maleate and 13% maleic acid).

Every swatch is left on for 10 minutes at room temperature.

Directly on the swatches and without rinsing, the neutralizing treatment is repeated in the same way, leaving on for other 10 minutes, for total 20 minutes.

After the left on period, the formulation in excess is rinsed with running water and the curlers are dried with a drier for 30 minutes.

The swatches are removed from the curlers, and the deviousness of the curls is examined by photos.

After that, the swatches are carefully washed with a 15% solution of Sodium laureth-2 sulfate (Zetesol Les2/SL®) at a pH of 7.5. One gram of surfactant solution per swatch is weighted, directly applied on the swatch, massaged for 10 seconds and rinsed 10 times in a beaker with water.

This rinsing operation is repeated 40 times without drying during the different steps of rinsing.

Then, the swatches are dried (only after the last rinsing), according to this procedure:

I. The towel dried swatches are applied to a small head and dried on air at room temperature.

II. Afterwards, skilled personnel evaluates the deviousness of the curls

Conclusion:

The permanent system added with On Protection is believed to better maintain the deviousness of the curls after repeated washings, in comparison with other treatments.

In a lower ranking, the swatches treated with Olaplex® Bond Multiplier No 1 added to Bouclè Biowaving System Extra Delicate Neutralizer and the single Bouclè Biowaving System Extra Delicate Neutralizer, maintain the deviousness of the curls in a similar way.

Finally, the swatches treated with Liposol maleate and maleic acid added to Bouclè Biowaving System Extra Delicate Neutralizer maintain the deviousness of the curls in a lower degree.

EXAMPLE 9

A Reducing Treatment: Hair Conditioning

Four hair samples from a human subject, standard weight and width and level 5, are colored with Davines Mask with Vibrachrom 3.51.

The coloring formulation was applied mixed with Davines Activator 20 vol., hydrogen peroxide emulsion, according to the Davines operating manual, in a 1:1.5 ratio.

The color was carefully applied in a quantity sufficient to color all the fibers of the swatches, then left on for 35 minutes at room temperature.

After that, the swatches were carefully rinsed with SOLU shampoo of the Essential Hair Care Davines line, in order to eliminate the excess color.

5 grams per swatch of the reducing formulation Davines Balance Curling System #1 are applied on the wet and towel dried swatches, and left on for 30 minutes.

After the left on period, the swatches are washed with water and ready to be treated with:

1) 5 g of maleic 2% water solution,
2) 5 g Liposol Maleate (Sabinsa Corporation) 2% water solution,
3) 5 g Olaplex® Bond Multiplier No 1, 2% water solution,
4) 5 g On protection (7% liposol maleate and 13% maleic acid) 10% water solution.

All the swatches are left on at room temperature for 7.30 minutes.

This treatment is repeated without rinsing, directly on the swatches, for 7.30 minutes (overall 15 minutes).

After the left on time, the swatches are rinsed with running water to eliminate the excess product.

Then, the swatches are carefully washed with a Sodium Laureth-2 sulfate (Zetesol Les 2/SL®) 15% and to a pH of 7.5. 1.5 grams of the surfactant solution per gram of swatch, are directly applied to the swatches, massaged for 10 seconds and rinsed 10 times in a beaker containing 100 g water.

This operation is repeated 5 times for every swatch.

At the end of the 5 washings, the swatches are carefully rinsed only with water and dried with an airdryer, for appreciating the chromatic differences and evaluate the hair appearance after this treatment.

Results:

Hair looks healthy, soft and hydrated. In relation to softness and silkiness, skilled technicians regard as preferred the swatch treated with only Liposol maleate 2%, then the swatch treated with On Protection 2% and the swatch treated with Olaplex® Bond Multiplier No 1, 2%. The swatch treated with maleic acid is the last.

EXAMPLE 10

Improvement of the Sensory Properties of Hair Treated With a Reducing Treatment After Coloring Four swatches of level 7 natural hair, standard weight and width, are bleached two times using the Davines Mask Hair Bleaching Powder mixed with an activator, hydrogen peroxide emulsion, Davines Activator 40 vol. in a 1:2 ratio.

The above described mixture is applied on single swatches in order to obtain a homogenous distribution of the product on the hair fibers.

The swatches are covered with an aluminum foil and left on for 50 minutes at room temperature. At the end of the left on period, the swatches are rinsed and carefully washed with a shampoo of the Davines Essential Hair Care SOLU line and dried. The entire process is repeated two times until to obtain the lightening level 11 according to Davines Color Manual.

The swatches as above treated are colored with Davines Mask with Vibrachrom 10.01 mixed with Davines Activator 20 vol. in a ratio 1:1.5 as disclosed in the Davines manual.

The coloration was applied to every swatch in an amount to obtain an homogeneous distribution of the product on all the hair fibers of the single swatch.

At the end of the coloration step, after rinsing with shampoo SOLU of the Essential Hair Care line of Davines and drying, the swatches are treated with 5 g of the Davines reducing formulation called Balance Curling System #1 and left on for 30 minutes at room temperature.

Then, the swatches are rinsed with water and treated as follows:
1) 5 g maleic acid 2% water solution,
2) 5 g Liposol maleate (Sabinsa Corp.) 2% water solution,
3) 5 g Olaplex® Bond Multiplier No 1, 2% water solution,
4) 5 g On Protection (7% Liposol maleate and 13% maleic acid) 2% water solution.

These treatments are left on for 7.30 minutes.

Without rinsing and directly on the swatches, the treatment is repeated in the same conditions for further 7.30 minutes for a total treatment time of 15 minutes.

After the left on period, the excess product is washed with running water.

Then, the swatches are carefully washed with a Sodium Laureth-2 sulfate (Zetesol Les 2/SL®) 15% and to a pH of 7.5. 1.5 grams of the surfactant solution per gram of swatch, are directly applied to the swatches, massaged for 10 seconds and rinsed 10 times in a beaker containing 100 g water.

Finally, the swatches are carefully washed in order to appreciate the chromatic differences.

Results:

The swatches treated with On Protection, liposol maleate, maleic acid and Olaplex® Bond Multiplier No 1, do not present significant chromatic differences, showing a similar color retention.

The qualitative evaluation with reference to the sensory appearance of the swatches points out that the swatch treated with On Protection is slightly smoother and silkier than the swatches treated with other products; this is particularly evident in the terminal part, where the swatch treated with On Protection appears more intact and compact than all the other swatches. Finally, the increased compactness of the hair stem treated with On Protection gives rise to a greater aptitude to reflect light and, consequently, to a greater overall brightness.

Photographs of the swatches treated according to this procedure are available at Davines Research and Development Laboratories.

EXAMPLE 11

Bleaching Treatment: Improvement of the Color Retention and Hair Sensoriability

Five hair samples from a human subject having a standard weight and a width and level 7 are colored with a Davines Mask with Vibrachrom 3.51. The coloring formulation was applied mixed with Davines Activator 20 vol., hydrogen peroxide emulsion, according to Davines operating manual, in a 1:1.5 ratios. The color was carefully applied in a quantity sufficient to give a homogeneous color to all fibers of the swatches. The mixture was left on for 35 minutes at room temperature.

After that, the swatches were carefully rinsed with shampoo Davines SOLU of the Essential Hair Care line, in order to eliminate the excess color.

After the left on period, the swatches were treated with the following reducing compositions:
1) 100 ml Davines Balance Curling System #1
2) 100 ml Davines Balance Curling System #1 added with 1.8 ml of a 20% maleic acid water solution,
3) 100 ml Davines Balance Curling System #1 added with 1.8 ml of a liposol maleate (Sabinsa Corp.) 20% water solution,
4) 100 ml Davines Balance Curling System #1 added with 1.8 ml of Olaplex® Bond Multiplier No 1,
5) Davines Balance Curling System #1 added with 1.8 ml of On Protection (12% liposol maleate and 8% maleic acid).

On the wet and towel dried swatches, 5 grams of the above described reducing formulations are applied per swatch, and then left on for 30 minutes.

After the left on period, the swatches are washed with hot running water for 1 minute and left 10 minutes towel dried on air without any treatment, in order to stabilize the treatment.

Five neutralizing solutions are prepared:
1) 100 ml of a neutralizing solution (Davines Bouclè Biowaving System Extra Delicate Neutralizer hydrogen peroxide 2.1%),
2) 100 ml of the neutralizing solution Davines Bouclè Biowaving System Extra Delicate Neutralizer 1 added with 1.8 ml of a 20% maleic acid water solution,
3) 100 ml of a neutralizing solution Davines Bouclè Biowaving System Extra Delicate Neutralizer 1 added with 1.8 ml of a 20% liposol maleate water solution,
4) 100 ml of a neutralizing solution Davines Bouclè Biowaving System Extra Delicate Neutralizer 1 added with 1.8 ml of Olaplex® Bond Multiplier No 1, 5) 100 ml of a neutralizing solution Davines Bouclè Biowaving System Extra Delicate Neutralizer 1 added with 1.8 ml of On Protection (12% liposol maleate and 8% maleic acid in water solution).

The swatches are left on for 10 minutes at room temperature.

Without rinsing, directly on the swatches, the application of the neutralizing solutions is repeated according to the same procedure for other 10 minutes, totally 20 minutes for the application of the neutralizing solutions.

After the left on period, the excess product is washed away and the swatches are treated with 5 grams of the following solutions and left on for 7.5 minutes:

1) 45 ml water,
2) 3 g maleic acid in 45 ml water,
3) 3 g of liposol maleate in 45 ml water,
4) 15 ml of Olaplex® Bond Multiplier No 1 in 45 ml water,
5) 15 ml of On Protection (12% liposol maleate and 8% maleic acid) in 45 ml water.

After the left on period, all the swatches are washed with Davines SOLU shampoo of the Essential Hair Care and then treated with the Davines Momo Conditioner of the Essential Hair Care line for 5 minutes.

Finally, the swatches are washed and dried.

Results:

The swatches were evaluated from skilled technicians as follows:

The swatches treated with On Protection (12% liposol maleate and 8% maleic acid in water solution) and with liposol maleate are more intensive and vibrating, showing an increased aptitude to retain the color after the reducing treatment. On the contrary, the swatches treated with Olaplex® Bond Multiplier No 1 and with maleic acid are chromatically weaker and similar to the swatch without protective agents.

Photographs of the swatches treated according to this procedure are available at Davines Research and Development Laboratories.

EXAMPLE 12

Hair Resistance to Reducing Treatment

Five level 5 natural hair swatches, weight and width standard, are washed with Essential Hair Care SOLU shampoo.

Then, the swatches are towel dried with adsorbing paper for removing excess water and subsequently enrolled on 1 cm diameter curlers.

2 ml of Davines Balance Curling System #1 perm are applied on all the curlers using a spout dispenser and left on for 30 minutes.

After that, every curler is rinsed with abundant water for 1 minute using cold running water.

Then, the swatches are neutralized using different neutralizing solutions:

2.5 g Davines Bouclè Biowaving System Extra Delicate Neutralizer (hydrogen peroxide 2.1%), 2.5 g maleic acid, 2% water solution, 2.5 g liposol maleate (Sabinsa Corp.) 2% water solution, 2.5 g Olaplex® Bond Multiplier No 1, 10% water solution, 2.5 g On Protection (12% liposol maleate and 8% maleic acid) 10% water solution.

The swatches are left on for 7.30 minutes at room temperature.

Without rinsing, directly on the swatches, the application of the neutralizing solutions is repeated according to the same procedure for other 7.30 minutes, totally 15 minutes.

After the left on period, the excess product is rinsed with cold running water and the curlers are dried in an oven ISCO at 53° C.±1 for 4 hours.

The swatches are removed from the curlers and the curl sinuosity is evaluated using a camera.

Then, the swatches are carefully washed with a Sodium Laureth-2 sulfate (Zetesol Les 2/SL®) 15% and to a pH of 7.5. 1.0 grams of the surfactant solution per gram of swatch, is directly applied to the swatch, massaged for 30 seconds and rinsed 10 times in a beaker with water.

This washing operation is repeated 40 times without drying after each rinsing step.

The swatches are naturally dried on air.

Then, the tensile strength was evaluated.

The Tensile Strength Test was made with using a dynamometer Texture Analysis Plus (Extended Height) using pneumatic clamps.

The tensile strength of hair treated with different compositions was compared with the tensile strength of the swatch neutralized only with Davines Bouclè Biowaving System Extra Delicate Neutralizer.

| SAMPLE | TENSILE STRENGTH (N) |
| --- | --- |
| Davines Bouclé Biowaving System Extra Delicate Neutralizer | 0.93 ± 0.1 |
| On Protection | 1.0 ± 0.08 |
| Liposol Maleate | 1.04 ± 0.16 |
| Olaplex ® Bond Multiplier No1 | 0.73 ± 0.12 |
| Maleic acid | 1.01 ± 0.03 |

Conclusions:

The swathes treated with On Protection, Liposol maleate and maleic acid are more protected in comparison with those treated with Olaplex® Bond Multiplier No 1 and Davines Bouclè Biowaving System Extra Delicate Neutralizer.

FINAL CONCLUSIONS

According to the above examples, these conclusions may be drawn:

It is clearly shown that the linking compositions of the present invention can successfully protect hair from potential oxidative and photo-oxidative damages. This assertion is based on Examples 2 ad 3, where different mixtures of liposol maleate and maleic acid are used for the color protection of previously colored natural swatches, in an event also after repeated washing steps and also a subsequent exposition to UV radiations.

The results using the mixture liposol maleate+maleic acid are better than the single components, maleic acid and liposol maleate, and also than the reference commercial product Olaplex® Bond Multiplier No 1. Then, a synergic effect between maleic acid and liposol maleate in the hair protection is evident.

It is confirmed that the protective action of the hair color after repeated washing steps is better than the single components, maleic acid and liposol maleate, and also than the reference commercial product Olaplex® Bond Multiplier No 1. The protective effect of the cosmetic coloring is disclosed also in Example 11, when the treatment with linking formulations according to the present invention is carried out after the application of a reducing treatment.

The hair structure protection to bleaching treatments conferred by the linking compositions according to the present invention is confirmed in different examples regarding both the tensile strength tests (example 5 and 7) and the sensorial evaluations of the swatches also treated with repeated bleaching steps as in example 6.

The linking formulations according to the present invention are also able, during reducing treatments, to protect the hair structure giving softness and elasticity to hair as well as conferring a greater tensile strength.

Figure 1:
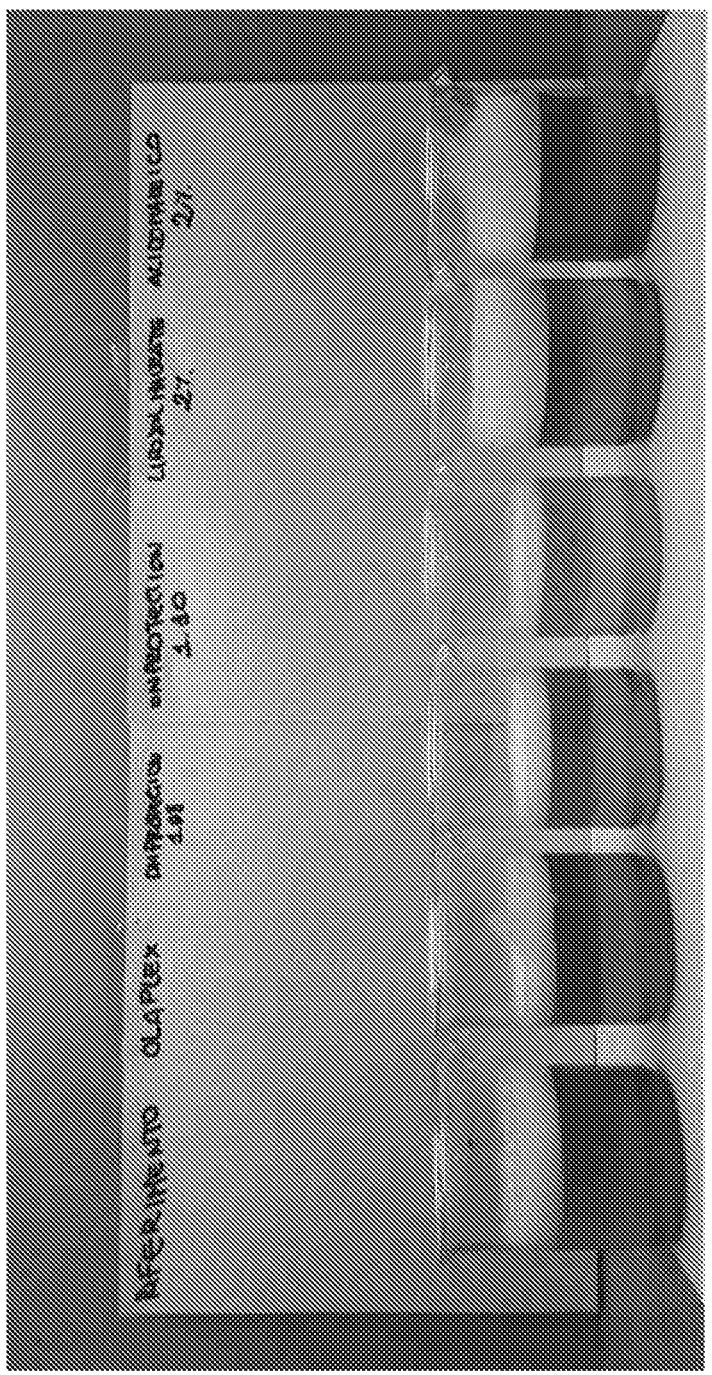
FIG. 1 shows different rinsing waters in a test of color fastness to washing in one embodiment of the invention.
Figure 2:
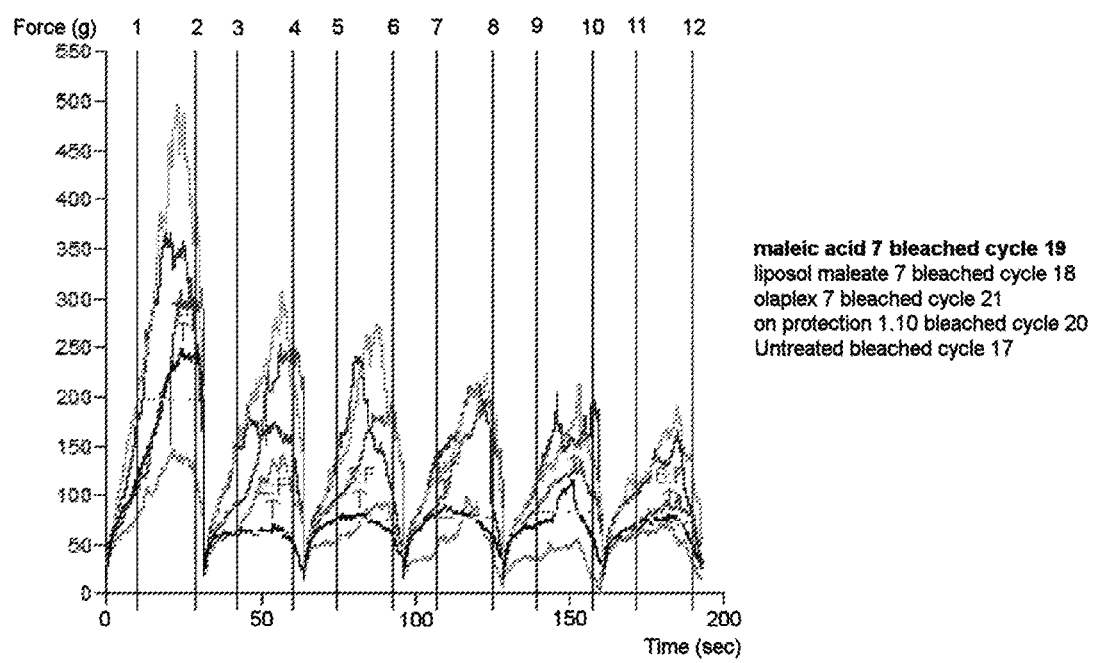
FIG. 2 shows graphs of the force exerted by a brush for combing six times a swatch in one embodiment of the invention.

The invention claimed is:

1. A formulation consisting of:
   a binding agent;
   an aqueous solvent; and
   one or more cosmetically acceptable excipients,
   wherein the binding agent is
   a mixture of liposol maleate and maleic acid, a weight ratio between the liposol maleate and the maleic acid being from 5:95 to 95:5.

2. The formulation according to claim 1, wherein the mixture consists of liposol maleate and maleic acid having a weight ratio from 10:90 to 80:20.

3. The formulation according to claim 1, wherein the mixture consists of liposol maleate and maleic acid having a weight ratio 35:65.

4. The formulation according to claim 1, wherein the mixture consists of liposol maleate and maleic acid having a weight ratio 60:40.

5. The formulation according to claim 1, wherein the one or more cosmetically acceptable excipients are selected from the group consisting of water, surfactants, vitamins, natural extracts, chelating agents, perfumes, antioxidants, hair coloring agents, proteins, amino acids, humectants, emollients, penetrants, thickeners, viscosity modifiers, hair fixatives, film formers, emulsifiers, opacifying agents, propellants, carriers, salts, pH adjusting agents, neutralizing agents, stabilizers, buffers, hair conditioning agents, anti-static agents, anti-frizz agents, anti-dandruff agents, and a combination thereof.

* * * * *